United States Patent [19]

Clark

[11] Patent Number: 6,051,573
[45] Date of Patent: Apr. 18, 2000

[54] TREATMENT OF GLC1A GLAUCOMA WITH NON-STEROIDAL GLUCOCORTICOID ANTAGONISTS

[75] Inventor: Abbot F. Clark, Arlington, Tex.

[73] Assignee: Alcon Laboratories, Inc., Fort Worth, Tex.

[21] Appl. No.: 08/994,957

[22] Filed: Dec. 19, 1997

Related U.S. Application Data

[63] Continuation-in-part of application No. 08/858,298, May 19, 1997, abandoned, which is a continuation-in-part of application No. 08/631,041, Apr. 12, 1996, abandoned, which is a continuation of application No. 08/268,086, Jun. 28, 1994, abandoned.

[51] Int. Cl.[7] .................. A61K 31/535; A01N 43/60; A01N 43/40; A01N 43/64; A01N 43/36

[52] U.S. Cl. .................. 514/235.5; 514/239.2; 514/255; 514/333; 514/340; 514/341; 514/343; 514/359; 514/424; 514/425; 514/427; 514/428; 514/408

[58] Field of Search .................. 514/235.5, 239.2, 514/255, 333, 340, 341, 343, 359, 424, 425, 427, 428, 408

[56] References Cited

U.S. PATENT DOCUMENTS

| | | | |
|---|---|---|---|
| 4,296,206 | 10/1981 | Simons, Jr. | 435/240 |
| 4,395,404 | 7/1983 | Low et al. | 424/177 |
| 4,861,580 | 8/1989 | Janoff et al. | 424/1.1 |
| 5,606,043 | 2/1997 | Nguyen et al. | 536/23.5 |

FOREIGN PATENT DOCUMENTS

| | | |
|---|---|---|
| 536182 | 4/1993 | European Pat. Off. . |
| 93039925 | 6/1993 | Japan . |
| WO 94/18967 | 9/1994 | WIPO .......... A61K 31/415 |

OTHER PUBLICATIONS

"Ketoconazole Binds to Glucocorticoid Receptors and Exhibits Glucocorticoid Antagonist Activity in Cultured Cells", Loose et al., J. Clin. Invest., vol. 72, 1983, pp. 404–408.

"Steroids, Ocular Hypertension, and Glaucoma", Abbot F. Clark, Ph.D., Journal of Glaucoma, vol. 4, Oct. 1995, pp. 354–369.

Sommer A, et al. Relationship between intraocular pressure and primary open angle glaucoma among white and black Americans. Arch. Ophthalmol. 109:1090–1095, (1991).

Sheffield, et al., "Genetic Linkage of Familial Open Angle Glaucoma to Chromosome 1q21–q31," Nature Genetics, 4:47–50 (1993).

Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995).

Akarsu, et al., "A Second Locus (GLC3B) for Primary Congenital Glaucoma (Buphthalmos) Maps to the 1p36 Region," Human Molecular Genetics, 5(8):1199–1203 (1996).

Stoilova, et al., "Localization of a Locus (GLC1B) for Adult–Onset Primary Open Angle Glaucoma to the 2cen–q13 Region," Genomics, 36:142–150 (1996).

Wirtz, et al., "Mapping a Gene for Adult–Onset Primary Open–Angle Glaucoma to Chromosome 3q," Am. J. Hum. Genet., 60:296–304 (1997).

Andersen, et al., "A Gene Responsible for the Pigment Dispersion Syndrome Maps to Chromosome 7q35–q36," Arch. Ophthalmol., 115:384–388 (1997).

Richards, et al., "Mapping of a Gene for Autosomal Dominant Juvenile–Onset Open–Angle Glaucoma to Chromsome 1q," Am. J. Hum. Genet., 54:62–70 (1994).

Morissette, et al., "A Common Gene for Juvenile and Adult–Onset Primary Open–Angle Glaucomas Confined on Chromosome 1q," Am. J. Hum. Genet., 56:1431–1442 (1995).

Wiggs, et al., "Genetic Linkage of Autosomal Dominant Juvenile Glaucoma to 1q21–q31 in Three Affected Pedigrees," Genomics, 21:299–303 (1994).

Meyer, et al., "Age–Dependent Penetrance and Mapping of the Locus for Juvenile and Early–Onset Open–Angle Glaucoma on Chromosome 1q (GLC1A) in a Frence Family," Hum. Genet., 98:567–571 (1996).

Graff, et al., "Confirmation of Linkage to 1q21–31 in a Danish Autosomal Dominant Juvenile–Onset Glaucoma Family and Evidence of Genetic Heterogeneity," Hum. Genet., 96:285–289 (1995).

Stone, et al., "Identification of a Gene That Causes Primary Open Angle Glaucoma," Science, 275:668–670 (1997).

Polansky, et al., "Eicosanoid Production and Glucocorticoid Regulatory Mechanisms in Cultured Human Trabecular Meshwork Cells," The Ocular Effects of Prostaglandins and Other Eicosanoids, pp. 113–138 (1989).

Polansky, et al., "In Vitro Correlates of Glucocorticoid Effects on Intraocular Pressure," Glaucoma Update IV (1991).

Polansky, et al., "Cellular Pharmacology and Molecular Biology of the Trabecular Meshwork Inducible Glucocorticoid Response Gene Product," Ophthalmologica, 211:126–139 (1997).

Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," FEBS Letters, 413:349–353 (1997).

(Kubota, et al., "A Novel Myosin–like Protein (Myocilin) Expressed in the Connecting Cilium of the Photoreceptor: Molecular Cloning, Tissue Expression, and Chromosomal Mapping," Genomics, 41:360–369 (1997).

Sunden, et al., "Fine Mapping of the Autosomal Dominant Juvenile Open Angle Glaucoma (GLC1A) Region and Evaluation of Candidate Genes," Genome Research, 6:862–869 (1996).

(List continued on next page.)

*Primary Examiner*—Jose' G. Dees
*Assistant Examiner*—Alton Pryor
*Attorney, Agent, or Firm*—Sally Yeager

[57] ABSTRACT

Compositions of non-steroidal glucocorticoid antagonists for treating GLC1A glaucoma and methods for their use are disclosed.

4 Claims, No Drawings

OTHER PUBLICATIONS

Adam, et al., "Recurrent Mutations in a Single Exon Encoding the Evolutionarily Conserved Olfactomedin–Homology Domain of TIGR in Familial Open–Angle Glaucoma," Human Molecular Genetics, 6(12):2091–2097 (1997).

Kass, et al., "Corticosteroid–Induced Glaucoma, In Ritch, R., Shields, M. B., Krupin, T. (eds.)," The Glaucomas, The C. V. Mosby Company, St. Louis, MO, pp. 1161–1168 (1989).

De Santis, et al., Dexamethasone–Induction of Ocular Hypertension in the Primate, ARVO Abstracts. Invest. Ophthalmol. Vis. Sci., 31(Suppl.):99 (1990).

Knepper, et al., "Intraocular Pressure and Glycosaminoglycan Distribution in the Rabbit Eye: Effect of Age and Dexamethasone," Exp. Eye Res., 27:567–575 (1978).

Francois, et al., Ultrastructural and Morphometric Study of Corticosteroid Glaucoma in Rabbits, Ophthalmic Res., 16:168–178 (1984).

Lorenzetti, O. J., "Effects of Corticosteroids on Ocular Dynamics in Rabbits," J. Pharmacol. Exp. Therap., 175:763–772 (1970).

Zhan, et al., "Steroid Glaucoma: Corticosteroid–Induced Ocular Hypertension in Cats," Exp. Eye Res., 54:211–218 (1992).

Rozsival, et al., "Aqueous Humour and Plasma Cortisol Levels in Glaucoma and Cataract Patients," Current Eye Research, 1:391–396 (1981).

Ray, et al., "Plasma Cortisol in Glaucoma," Ann. Ophthalmol., 9:1151–1154 (1977).

Schwartz, et al., "Increased Plasma Free Cortisol in Ocular Hypertension and Open Angle Glaucoma," Arch. Ophthalmol., 105:1060–1065 (1987).

Wilson, et al., Dexamethasone Induced Ultrastructural Changes in Cultured Human Trabecular Meshwork Cells, Cur. Eye Res., 12:783–793 (1993).

Clark, et al., "Glucocorticoid–Induced Formation of Cross–Linked Actin Networks in Cultured Human Trabecular Meshwork Cells," Invest. Ophthalmol. Vis. Sci., 35:281–294 (1994).

Loose, et al., "Ketoconazole Binds to Glucocorticoid Receptors and Exhibits Glucocorticoid Antagonist Activity in Cultured Cells," J. Clin. Invest., 72:404–408 (1983).

TREATMENT OF GLC1A GLAUCOMA WITH NON-STEROIDAL GLUCOCORTICOID ANTAGONISTS

This application is a continuation-in-part of U.S. patent application Ser. No. 08/858,298 filed May 19, 1997 now abandoned, which is a continuation of U.S. patent application Ser. No. 08/631,041 filed Apr. 12, 1996 now abandoned, which is a continuation of U.S. patent application Ser. No. 08/268,086 filed Jun. 28, 1994 now abandoned.

This invention is directed to the use of non-steroidal glucocorticoid antagonists for treating glaucoma or ocular hypertension resulting from altered expression of the GLC1A gene (hereinafter GLC1A or 1q glaucoma) in an individual.

BACKGROUND OF THE INVENTION

The glaucomas are a heterogeneous group of optic neuropathies characterized by cupping of the optic nerve head, thinning of the retinal nerve fiber layer due to loss of retinal ganglion cells, and specific pathognomonic changes in visual fields. Elevated intraocular pressure (IOP) is a very important risk factor for the development of most common forms of glaucoma (Sommer A, et al. Relationship between intraocular pressure and primary open angle glaucoma among white and black Americans. Arch. Ophthalmol. 109:1090–1095,1991).

A family history of glaucoma also is an important risk factor for the development of glaucoma. It appears that a significant portion of glaucoma is inherited (or at least the risk for developing glaucoma is inherited) although it is often difficult to establish clear inheritance patterns for most of the glaucomas because of the disease onset late in life and the slowly progressive clinical manifestations of the disease. Despite these problems, a number of families with heritable forms of glaucoma have been identified and these families have been used to map a variety of glaucoma genes (Sheffield, et al., "Genetic Linkage of Familial Open Angle Glaucoma to Chromosome 1q21 -q31," *Nature Genetics,* 4:47–50 (1993); Sarfarazi, et al., "Assignment of a Locus (GLC3A) for Primary Congenital Glaucoma (Buphthalmos) to 2p21 and Evidence for Genetic Heterogeneity," *Genomics,* 30:171–177 (1995); Akarsu, et al., "A Second Locus (GLC3B) for Primary Congenital Glaucoma (Buphthalmos) Maps to the 1p36 Region," *Human Molecular Genetics,* 5(8):1199–1203 (1996); Stoilova, et al., "Localization of a Locus (GLC1B) for Adult-Onset Primary Open Angle Glaucoma to the 2cen-q13 Region," *Genomics,* 36:142–150 (1996); Wirtz, et al., "Mapping a Gene for Adult-Onset Primary Open-Angle Glaucoma to Chromosome 3q," *Am. J Hum. Genet.,* 60:296–304 (1997); Andersen, et al., "A Gene Responsible for the Pigment Dispersion Syndrome Maps to Chromosome 7q35-q36," *Arch. Ophthalmol.,* 115:384–388 (1997)). The first glaucoma gene mapped (GLC1A) was in a large family with autosomal dominant inherited juvenile glaucoma (JG). This disease is characterized by an early disease onset (late teens to early 20s), relatively high IOPs, and general resistance to conventional pharmacological IOP lowering therapy. The GLC1A gene was mapped by positional cloning and linkage analysis to chromosome 1q22-q25 (Sheffield et al, Id.) and a number of other groups have confirmed the 1q location of this juvenile glaucoma gene (Richards, et al., "Mapping of a Gene for Autosomal Dominant Juvenile-Onset Open-Angle Glaucoma to Chromosome 1q," *Am. J. Hum. Genet.,* 54:62–70 (1994); Morissette, et al., "A Common Gene for Juvenile and Adult-Onset Primary Open-Angle Glaucomas Confined on Chromosome 1q," *Am. J. Hum. Genet.,* 56:1431–1442 (1995); Wiggs, et al., "Genetic Linkage of Autosomal Dominant Juvenile Glaucoma to 1q21-q31 in Three Affected Pedigrees," *Genomics,* 21:299–303 (1994); Meyer, et al., "Age-Dependent Penetrance and Mapping of the Locus for Juvenile and Early-Onset Open-Angle Glaucoma on Chromosome 1q (GLC1A) in a French Family," *Hum. Genet.,* 98:567–571 (1996); Graff, et al., "Confirmation of Linkage to 1q21-31 in a Danish Autosomal Dominant Juvenile-Onset Glaucoma Family and Evidence of Genetic Heterogeneity," *Hum. Genet.,* 96:285–289 (1995)). Glaucoma due to the GLC1A gene is often referred to as 1q glaucoma.

The GLC1A gene was identified as encoding a 57 kD protein expressed in the trabecular meshwork (TM) (Stone, et al., "Identification of a Gene That Causes Primary Open Angle Glaucoma," *Science,* 275:668–670 (1997)). The expression of the GLC1A gene, and the encoded TM protein, is up-regulated by glucocorticoids (Polansky, et al., "Eicosanoid Production and Glucocorticoid Regulatory Mechanisms in Cultured Human Trabecular Meshwork Cells," *The Ocular Effects of Prostaglandins and Other Eicosanoids,* pp. 113–138 (1989); Polansky, et al., "In Vitro Correlates of Glucocorticoid Effects on Intraocular Pressure," *Glaucoma Update IV* (1991); and Polansky, et al., "Cellular Pharmacology and Molecular Biology of the Trabecular Meshwork Inducible Glucocorticoid Response Gene Product," *Ophthalmologica,* 211:126–139 (1997)). This TM protein is also known as TIGR (trabecular meshwork inducible glucocorticoid response) (Polansky, Id.). The glucocorticoid-induction of this TM protein has been suggested to be involved in the generation of glucocorticoid-induced ocular hypertension and glaucoma (Polansky, Id.).

The GLC1A gene is expressed in other ocular tissues such as the ciliary epithelium (Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," *FEBS Letters,* 413:349–353 (1997)) and the retina (Kubota, et al., "A Novel Myosin-like Protein (Myocilin) Expressed in the Connecting Cilium of the Photoreceptor: Molecular Cloning, Tissue Expression, and Chromosomal Mapping," *Genomics,* 41:360–369 (1997)). The gene is referred to by several names including GLCIA (Sheffield, supra; Sunden, et al., "Fine Mapping of the Autosomal Dominant Juvenile Open Angle Glaucoma (GLC1A) Region and Evaluation of Candidate Genes," *Genome Research,* 6:862–869 (1996); Stone, et al., supra), TIGR (Polansky supra; Ortego, supra), and myocilin (Kubota, supra). Mutations GLC1A are not only responsible for juvenile glaucoma, but also a significant subset of adult onset primary open angle glaucoma (Stone, et al., supra; Adam, et al., "Recurrent Mutations in a Single Exon Encoding the Evolutionarily Conserved Olfactomedin-Homology Domain of TIGR in Familial Open-Angle Glaucoma," *Human Molecular Genetics,* 6(12):2091–2097 (1997)). The 1q glaucoma gene (GLC1A, TIGR) is the subject of Nguyen, et al., U.S. Pat. No. 5,606,043, issued Feb. 25, 1997.

Glucocorticoids have been associated with the development of ocular hypertension and primary open angle glaucoma (Kass, et al., "Corticosteroid-Induced Glaucoma, In Ritch, R., Shields, M. B., Krupin, T. (eds.)," *The Glaucomas,* The C. V. Mosby Company, St. Louis, Miss., pp. 1161–1168 (1989); DeSantis, et al., "Dexamethasone-Induction of Ocular Hypertension in the Primate, *ARVO Abstracts. Invest. Ophthalmol. Vis. Sci.,* 31(Suppl.):99 (1990); Knepper, et al., "Intraocular Pressure and Glycosaminoglycan Distribution in the Rabbit Eye: Effect of Age and Dexamethasone," *Exp. Eye Res.*, 27:567–575 (1978); Francois, et al., "Ultrastructural and Morphometric Study of Corticosteroid Glaucoma in Rabbits, *Ophthalmic Res.*, 16:168–178 (1984); Lorenzetti, O. J., "Effects of Corticosteroids on Ocular Dynamics in Rabbits," *J. Pharmacol. Exp. Therap.*, 175:763–772 (1970); and Zhan, et al., "Steroid Glaucoma: Corticosteroid-Induced Ocular Hypertension in Cats," *Exp. Eye Res.*, 54:211–218 (1992)). Glaucoma patients have also been reported to have higher levels of the endogenous glucocorticoid, cortisol (Rozsival, et al., "Aqueous Humour and Plasma Cortisol Levels in Glaucoma and Cataract Patients," *Current Eye Research*, 1:391–396 (1981); Ray, et al., "Plasma Cortisol in Glaucoma," *Ann. Ophthalmol.*, 9:1151–1154 (1977); and Schwartz, et al., "Increased Plasma Free Cortisol in Ocular Hypertension and Open Angle Glaucoma," *Arch. Ophthalmol.*, 105:1060–1065 (1987)).

It is known that trabecular meshwork cells have glucocorticoid receptors and that glucocorticoid binding with these receptors causes a change in trabecular meshwork cell gene expression. Known manifestations of this change include a reorganization of the cytoskeleton (Wilson, et al., "Dexamethasone Induced Ultrastructural Changes in Cultured Human Trabecular Meshwork Cells, *Cur. Eye Res.*, 12:783–793 (1993), and Clark, et al., "Glucocorticoid-Induced Formation of Cross-Linked Actin Networks in Cultured Human Trabecular Meshwork Cells," *Invest. Ophthalmol. Vis. Sci.*, 35:281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure is maintained or frequently occurs, the optic nerve head can be damaged resulting in the loss of visual field. Loss of visual field is the hallmark symptom associated with glaucoma.

Endogenous glucocorticoids may be responsible for producing the changes in the trabecular meshwork that lead to ocular hypertension and glaucoma. In the present case, it is believed that non-steroidal glucocorticoid antagonists bind to the glucocorticoid receptor in trabecular meshwork cells, and thereby prevent binding of endogenous glucocorticoids to the glucocorticoid receptor. They may also displace endogenous glucocorticoids which are bound to glucocorticoid receptors.

In summary, the GLC1A gene product can lead to the development of ocular hypertension and glaucoma in one of two ways: (1) mutations in GLC1A are responsible for most forms of juvenile glaucoma and a subset of adult onset POAG or (2) exposure of some individuals to glucocorticoids leads to increased GLC1A expression in the TM which causes increased aqueous humor outflow resistance and the development of ocular hypertension. The precise mechanism(s) responsible for GLC1A effects on IOP are currently unknown.

SUMMARY OF THE INVENTION

Non-steroidal glucocorticoid antagonists (NSGAs) and their pharmaceutical formulations are useful for treating GLC1A glaucoma. The invention is also directed to methods for controlling GLC1A glaucoma using NSGAs, some of which are novel.

DESCRIPTION OF THE PREFERRED EMBODIMENTS

Agents which alter the expression of GLC1A in the glaucomatous eye are expected to lower IOP and thereby prevent or inhibit the glaucomatous optic neuropathy which is being driven by elevated IOP. Glucocorticoids upregulte GLC1A expression in the TM of certain individuals. There have been several reports of elevated levels of the natural glucocorticoid cortisol in the aqueous humor and plasma of glaucoma patients (Schwartz, et al., supra; Rozsival, et al., supra). In addition, certain mutations in GLC1A may alter the expression of GLC1A in the TM tissue of 1q glaucoma patients. Unexpectedly, it has been discovered that certain non-steroidal glucocorticoid antagonists (NSGA) inhibit the expression of GLC1A in cultured human TM cells and lower elevated IOP in certain animal models of ocular hypertension. The NSGAs appear to work by inhibiting glucocorticoids from binding to the glucocorticoid receptor or displacing prebound steroids from the glucocorticoid receptor in the trabecular meshwork. The NSGAs thereby prevent the expression of GLC1A and the subsequent development of ocular hypertension.

Ketoconazole and clotrimazole are known glucocorticoid antagonists. (Loose, et al., "Ketoconazole Binds to Glucocorticoid Receptors and Exhibits Glucocorticoid Antagonist Activity in Cultured Cells," *J. Clin. Invest.*, 72:404–408 (1983)). They are not known to be useful in treating or controlling glaucoma.

Non-steroidal glucocorticoid antagonists which are particularly useful in treating GLC1A glaucoma have the following structure:

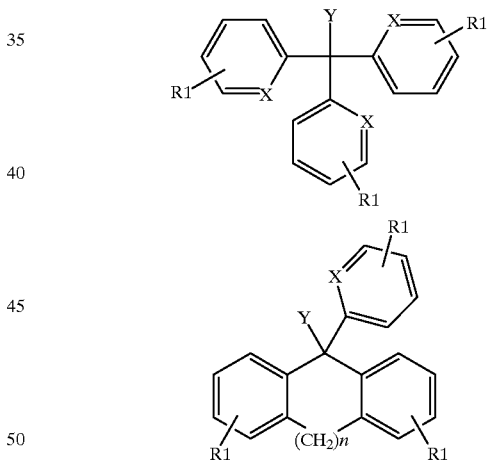

WHEREIN:
n=0,1,2;
X=CH or N;
R1=H, F, Cl, Br, R2, OR2, N(R2)$_2$, COOH, CONH$_2$, CONHR2, CON(R2)$_2$, CH$_2$N(CH$_2$CH$_2$)O;
R2=C$_1$–C$_6$ alkyl;
Y=N-imidazolyl, N-pyrrolidinyl, N-(2-hydroxymethyl) pyrrolidinyl, N-triazolyl, N-pyrazolyl each optionally substituted with CH$_3$, SH or S-C(4-Cl-C$_6$H$_4$)$_3$; OH, O(CH$_2$)$_2$N(CH$_2$CH$_2$)$_2$O, O(CH$_2$)$_2$N(CH$_2$CH$_2$)$_2$N (CH$_2$)$_2$OH;
and all pharmaceutically acceptable salts and esters.

Most preferred compounds include the following specific compounds:

(1)
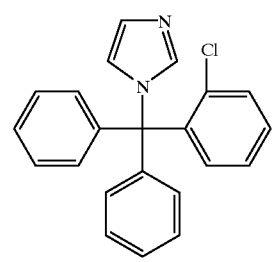
(2)
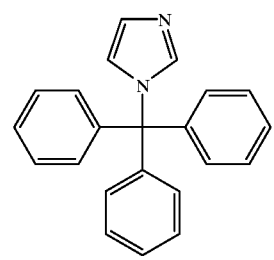
(3)
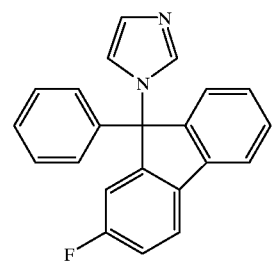
(4)
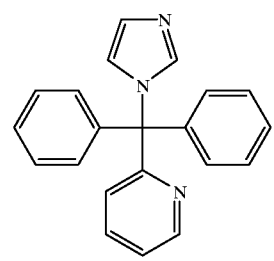
(5)
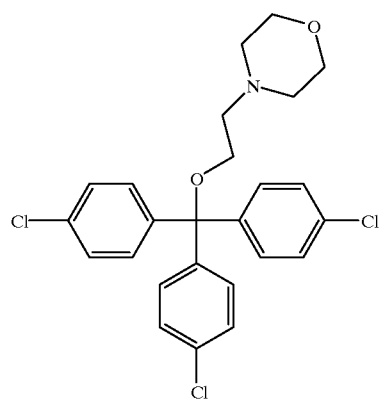
(6)
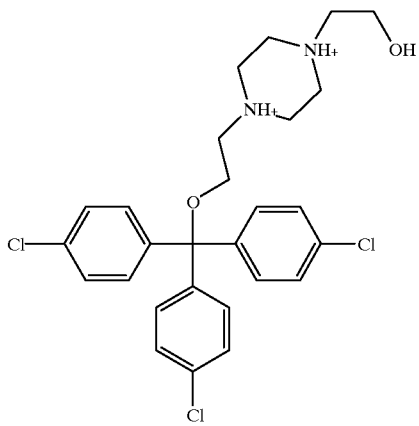
(7)
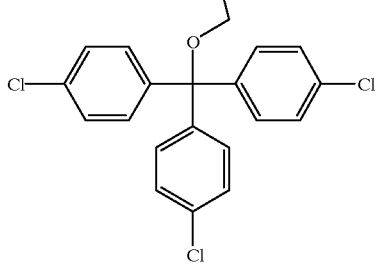
(8)
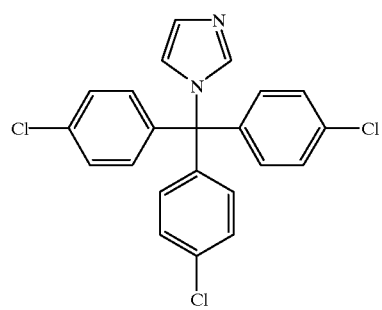
(9)
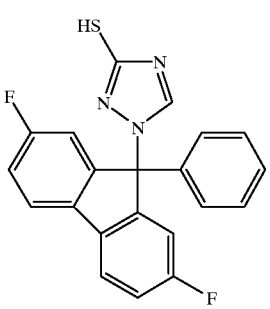

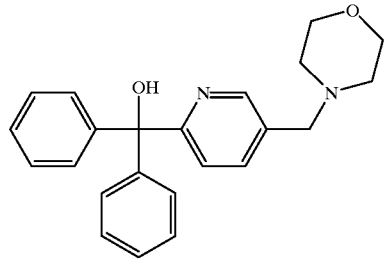
(10)

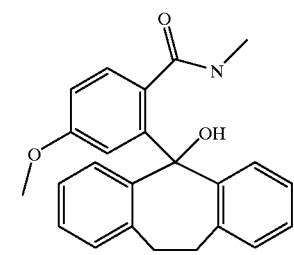
(11)

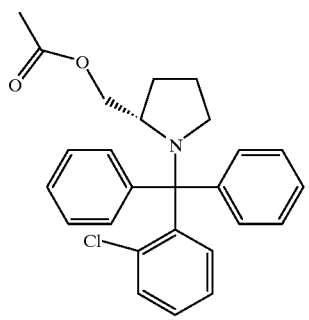
(12)

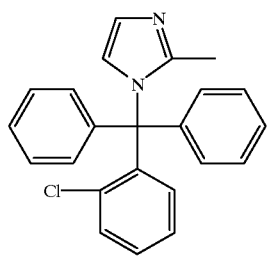
(13)

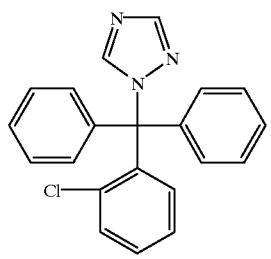
(14)

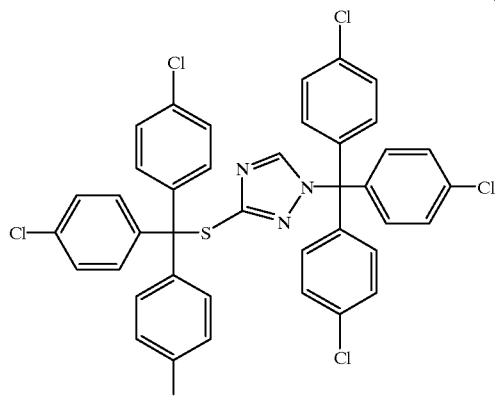
(15)

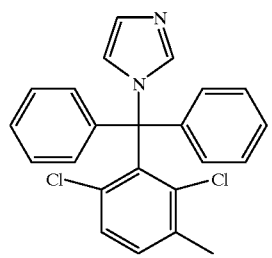
(16)

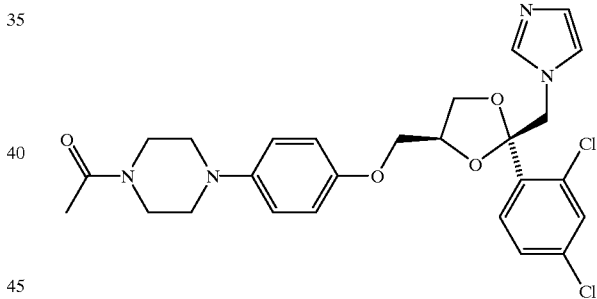
(17)

Names of Compounds
1 Clotrimazole
2 N-(Triphenylmethyl)imidazole
3 N-([2-Fluoro-9-phenyl]fluorenyl)imidazole
4 N-([2-Pyridyl]diphenylmethyl)imidazole
5 N-(2-[4,4',4''-Trichlorotrityl]oxyethyl)morpholine
6 1-(2[4,4',4''-Trichlorotrityl]oxyethyl)-4-(2-hydroxyethyl) piperazine dimaleate
7 N-([4,4',4'']-Trichlorotrityl)imidazole
8 9-(3-Mercapto-1,2,4-trazolyl)-9-phenyl-2,7-difluorofluorenone
9 1-(2-Chlorotrityl)-3,5-dimethylpyrazole
10 4-(Morpholinomethyl)-A-(2-pyridyl)benzhydrol
11 5-(5-Methoxy-2-(N-methylcarbamoyl)phenyl) dibenzosuberol
12 N-(2-Chlorotrityl)-L-prolinol acetate
13 1-(2-Chlorotrityl)-2-methylimidazole
14 1-(2-Chlorotrityl)-1,2,4-triazole
15 1, S-Bis(4,4',4''-trichlorotrityl)-1,2,4-triazole-3-thiol
16 N-((2,6-dichloro-3-methylphenyl)diphenyl) methylimidazole
17 Ketoconazole Topical formulations contain about 0.05 to 5 wt. % of a non-steroidal glucocorticoid antagonist. Systemic formulations contain about 10 to 1000 mg.

The formulations can be administered systemically or topically, preferably topically, one to four times daily according to the discretion of a skilled clinician.

The following examples are not meant to be limiting.

EXAMPLE 1

N-(Triphenylmethyl)imidazole (2)

A stirred suspension of triphenylmethanol (2.6 g, 10 mmol) and 1.36 g (20 mmol) of imidazole in 10 mL of HOAc was heated to 100° C. under $N_2$ for 1 h. The cooled mixture was diluted with $Et_2O$ and washed with water, saturated $Na_2CO_3$, water (until neutral), brine, dried ($MgSO_4$), filtered and concentrated. The crude product was purified by flash chromatography (110 g $SiO_2$, 25%–50% EtOAc-hexanes) to give 0.78 g (25%) of a solid. This was recrystallized from EtOAc to give 0.20 g of (2), m.p. 221°–223° C.

IR (KBr) 1489, 1443, 1210, 1072, 750, 701, 662 cm$^{-1}$.

NMR (CDCl$_3$): d 6.82, 7.07, 7.47 (all t, J=1, imidazole CH); 7.14 (m, 6H); 7.32 (m, 9H).

Anal. Calc'd ($C_{22}H_{18}N_2$): C, 85.13; H, 5.84; N, 9.03. Found: 85.16; 5.87; 9.02.

EXAMPLE 2

N-([2-Fluoro-9-phenyl]fluorenyl)imidazole (3)

a. To a stirred, ice-cooled solution of 2-fluorofluorenone (2.0 g, 10 mmol) in 15 mL of dry THF under $N_2$ was added 10 mL of 2.4 M phenyllithium solution in cyclohexane-$Et_2O$ (7:3), keeping T<20° C. The mixture was quenched with water and the product isolated with EtOAc and purified by flash chromatography (7% EtOAc-hexanes) to give 2.52 g (90%) of 2-fluoro-9-phenylfluoren-9-ol.

b. A solution of the above alcohol (0.57 g, 2.1 mmol) and imidazole (0.56 g, 8.4 mmol) in 6 mL of HOAc was heated to reflux under $N_2$ for 9.5 h. The crude product was isolated as described for (2) and purified by flash chromatography (30 g $SiO_2$, 50% EtOAc-hexanes) giving 0.40 g (59%) of a foam. This material was recrystallized from EtOAc to give 0.19 g of (3), m.p. 191.5°–194° C.

IR (KBr)1594, 1493, 1468, 1455, 1274, 1259, 1226, 1074, 862, 820, 766, 756, 744, 724, 702, 661 cmn$^{-1}$.

NMR (CDCl$_3$): d 6.95 (s, 1H); 7.0–7.5 (m, 12H); 7.7 (m, 2H).

Anal. Calc'd ($C_{22}H_{15}N_2F$): C, 80.96; H, 4.63; N, 8.59. Found: 80.93; 4.69; 8.53.

EXAMPLE 3

N-([2-Pyridyl]diphenylmethyl)imidazole (4)

A solution of diphenyl-2-pyridylmethanol (0.50 g, 1.9 mmol) and imidazole (0.50 g, 7.4 mmol) in 2 mL of EtCO$_2$H was heated to reflux under $N_2$ for 7 h. The crude product was isolated as described for (2) and purified by flash chromatography (60 g $SiO_2$, EtOAc) to give 0.08 g (13.5%) of a yellow solid. This material was further purified by trituration (4:1 hexanes-$Et_2O$) followed by recrystallization from EtOAc to give 0.03 g of (4), m.p. 214.5°–216.5° C.

IR (KBr) 1584, 1487, 1462, 1444, 1430, 1212, 1066, 760, 710, 702, 666 cm$^{-1}$.

NMR (CDCl$_3$): d 7.05 (m, 7H); 7.3 (m, 7H); 7.65 (m, 2H); 8.70 (d, J=4, further split, 1H).

Anal. Calc'd ($C_{21}H_{17}N_3$): C, 81.00; H, 5.50; N, 13.50. Found: 81.17; 5.50; 13.69.

EXAMPLE 4

N-([4,4',4"]-Trichlorotrityl)imidazole (7)

To a stirred solution of tris(4-chlorophenyl)methanol (0.36 g, 1.0 mmol) and imidazole (0.20 g, 2.9 mmol) in 2 mL of CH$_2$Cl$_2$ under $N_2$ at RT was added 0.40 mL (2.0 mmol) of trimethylsilyl triflate. After 1 h, the crude product was isolated as described for (2) and purified by flash chromatography (10% EtOAc-hexanes®EtOAc) to give 0.25 g of a semisolid. This material was triturated with 5% $Et_2O$-hexanes to give 0.20 g of (7) as a white solid, m.p. 153°–155° C.

IR (KBr) 1490, 1399, 1217, 1097, 1080, 1013, 815 cm$^{-1}$.

NMR (CDCl$_3$): d 6.77, 7.10, 7.41 (each s, 1H, imidazole CH); 7.04 (dt, 6H); 7.33 (dt, 6H).

Anal. Calc'd ($C_{22}H_{15}N_2Cl_3$): C, 63.86; H, 3.65; N, 6.77. Found: 63.96; 3.95; 6.70.

EXAMPLE 5

9-(3-Mercapto-1,2,4-trazolyl)-9-phenyl-2,7-difluorofluorenone (8)

a. To a stirred, ice-cooled suspension of 2,7-difluorofluorenone (1.45 g, 6.7 mmol) in 50 mL of dry THF under $N_2$ was added 3.0 mL of 3.0 M ethereal phenylmagnesium bromide. The solution was diluted with $Et_2O$ and washed with water, 0.5 M $H_2SO_4$, water (until neutral), brine, dried (MgSO$_4$), filtered and concentrated to give 1.99 g (100%) of an oil. This material was triturated (5% $Et_2O$-hexanes) giving 1.11 g (56%) of 2,7-difluoro-9-phenylfluoren-9-ol.

b. To a stirred solution of the above alcohol (1.10 g, 3.74 mmol) and 1,2,4-triazole-3-thiol (0.56 g, 5.5 mmol) in 4.5 mL of dry CH$_2$Cl$_2$ under $N_2$ was added 1.25 mL (10 mmol) of BF$_3$ etherate. After 20 min, the mixture was poured into saturated aqueous KH$_2$PO$_4$ and the crude product was isolated with EtOAc and purified by flash chromatography (100 g $SiO_2$, 10%(®)50% EtOAc-hexanes) giving 0.41 g of a solid. This material was recrystallized from MeOH to give 0.25 g of (8), m.p. 209°–211° C (dec).

IR (KBr) 1614 (w), 1595, 1466, 1436, 1259, 1210, 816, 740 cm$^{-1}$.

NMR (DMSO-d$_6$): d 7.2 (m, 7H); 7.5 (m, 2H); 7.83 (q, 2H); 8.28 (s, 1H, triazole CH); 14.0 (br s, 1H, SH).

Anal. Calc'd ($C_{21}H_{13}N_3F_2S$): C, 66.83; H, 3.47; N, 11.13. Found: 66.79; 3.84; 11.23.

EXAMPLE 6

1,S-Bis(4,4',4"-trichlorotrityl)-1,2,4-triazole-3-thiol (15)

The procedure of Example 5(b) was followed, using 1.26 g (3.47 mmol) of tris(4-chlorophenyl)methanol, 0.52 g (5.1 mmol) of 1,2,4-triazole-3-thiol, 4.0 mL of CH$_2$Cl$_2$ and 1.25 mL (10 mmol) of BF$_3$ etherate. Isolation followed by flash chromatography (75 g $SiO_2$, 40% EtOAc-hexanes) gave 0.51 g of the title compound, followed by 0.71 g of an unstable product that turned into the title compound upon standing in solution. A 0.44 g sample of the first-eluted material was recrystallized from MeOH giving 0.18 g of (15), m.p. 219°–221° C. (dec)

IR (KBr) 1490, 1399, 1257, 1097, 1013,815 cm$^{-1}$.

NMR (CDCl$_3$): d 6.75 (d, J=9, 6H); 7.05–7.3 (m, 18H); 7.59 (s, 1H).

Anal. Calc'd ($C_{40}H_{25}Cl_6N_3S$): C, 60.62; H, 3.18; N,5.30. Found: 60.72; 3.41; 5.23.

EXAMPLE 7

1-(2-Chlorotrityl)-3,5-dimethylpyrazole (9)

a. To a stirred, ice-cooled solution of 2-chlorobenzophenone (21.6 g, 100 mmol) in 150 mL of dry $Et_2O$ under $N_2$ was added 60 mL (120 mmol) of 2.0 M phenyllithium solution in cyclohexane-$Et_2O$ (7:3), keeping T<15° C. After stirring for a further 1 h at 15° C., the solution was poured onto crushed ice and extracted with $Et_2O$. The organic solution was washed with 0.2 M $H_2SO_4$, water (until neutral), brine, dried (MgSO$_4$), filtered and concentrated. The residue was recrystallized from hexanes containing a few per cent EtOAc to give 23.1 g (78%) of (2-chlorophenyl)diphenylmethanol as an off-white solid.

NMR (CDCl$_3$): d 4.43 (s, 1H, OH); 6.70 (dd, J=7.8 and 1.7, 1H); 7.11 (dt, J=7.8 and 1.5, 1H); 7.2–7.45 (m, 12H).

b. The above alcohol (4.20 g, 14.3 mmol) was dissolved in SOCl$_2$ (5.0 mL, 68 mmol) under N$_2$. The nitrogen line was replaced with a CaSO$_4$ drying tube. After a 1-min induction period, gas was rapidly evolved (CAUTION!). A further 3.4 mL (47 mmol) of SOCl$_2$ was added, followed by 4 mL of toluene. Stirring was continued for 6 h. The solution was then concentrated under reduced pressure, the residue dissolved in toluene, concentrated and vacuum pumped to give 4.40 g (99%) of (2-chlorophenyl) diphenylchloromethane as a solid.

NMR (CDCl$_3$): d 6.80 (dd, J=7.7 and 1.7, 1H); 7.10 (dt, J=7.3 and 1.5, 1H); 7.2–7.45 (m, 12H). This material contained 10% of the starting alcohol by NMR.

c. A solution of the above chloride (0.63 g, 2.0 mmol), 3,5-dimethylpyrazole (0.38 g, 4.0 mmol) and ethyldiisopropylamine (0.70 mL, 4.0 mmol) in dry DMF was stirred under N$_2$ for 16 h, then heated to 50° C. for 2 h. The mixture was poured into saturated Na$_2$CO$_3$ and the crude product isolated by EtOAc extraction and purified by flash chromatography (125 g SiO$_2$, 10% EtOAc-hexanes, then 50 g SiO$_2$, 5% EtOAc-hexanes) giving 0.18 g of a solid. This material was triturated with Et$_2$O, then recrystallized from EtOAc-MeOH to give 0.09 g of (9), m.p. 195°–197° C. IR (KBr) 1557, 1493, 1445, 1434, 1349, 1044, 906, 764, 746, 704, 696 cm$^{-1}$.

NMR (CDCl$_3$): d 1.40, 2.20 (each s, 3H); 5.90 (s, 1H, pyrazole CH); 7.0–7.5 (m, 14H).

Anal. Calc'd (C$_{24}$H$_{21}$N$_2$Cl): C, 77.30; H, 5.68; N, 7.51. Found: 77.42; 5.86; 7.46.

EXAMPLE 8
1-(2-Chlorotrityl)-2-methylimidazole (13)

A solution of the chloride of Example 7(b) (0.93 g, 3.0 mmol), 2-methylimidazole (0.50 g, 6.1 mmol) and ethyldiisopropylamine (1.1 mL, 6.3 mmol) in 5 mL of dry DMF was stirred at RT under N$_2$ for 2.5 h. The crude product was isolated by EtOAc extraction and purified by flash chromatography (100 g SiO$_2$, 70% EtOAc-hexanes) followed by spontaneous crystallization from EtOAc to give 0.6 g of (13), m.p. 177° C.

IR (KBr) 1492, 1444, 1432, 1397, 1238, 766, 753, 710 cm$^{-1}$.

NMR (CDCl$_3$): d 1.57 (s, 3H); 6.82 (d, 2H); 7.0–7.5 (m, 14H).

Anal. Calc'd (C$_{23}$H$_{19}$N$_2$Cl): C, 76.97; H, 5.34; N, 7.81. Found: 76.95; 5.49; 7.67.

EXAMPLE 9
1-(2-Chlorotrityl)-1,2,4-triazole (14)

The procedure described for (13) was followed, substituting 1,2,4-triazole (0.42 g, 6.1 mmol) for 2-methylimidazole. The crude product was recrystallized from acetone giving 0.6 g of (14), m.p. 160° C.

IR (KBr) 1497, 1446, 1434, 1277, 1142, 768, 751, 697 cm$^{-1}$.

NMR (CDCl$_3$): d 6.9 (d, 1H); 7.0–7.5 (m); 8.06 and 8.18 (each s, 1H).

Anal. Calc'd (C$_{21}$H$_{16}$N$_3$Cl): C, 72.93; H, 4.66; N, 12.15. Found: 72.95; 4.70; 12.07.

EXAMPLE 10
N-(2-Chlorotrityl)-L-prolinol acetate (12)

The procedure described for (13) was followed, using 1.47 g (4.7 mmol) of the chloride of Example 7(b), 0.55 g (5.5 mmol) of L-prolinol, 1.1 mL (6.3 mmol) of ethyldiisopropylamine and 10 mL of dry DMF. After 24 h, the crude product was isolated with EtOAc and purified by flash chromatography giving 0.84 g of a foam (major rotamer). A 0.30 g (0.79 mmol) sample of this material was acetylated (2 mL Ac$_2$O, 4 mL pyridine, RT, 16 h), the product was isolated (EtOAc) and recrystallized (MeOH) giving 0.24 g of (12), m.p. 102°–104° C.

IR (KBr) 1736, 1444, 1240, 1040, 756, 707 cm$^{-1}$.

NMR (CDCl$_3$): d 0.43 (m, 1H); 1.1–1.5 (3H); 2.00 (s, 3H); 2.8, 3.1 (AB, 2H, CH$_2$N); 3.5 (m, 1H, CHN); 3.9 (t, J=9,1H) and 4.05 (dd, 1H); 7.0–7.5 (m, 11H); 7.7 (dd, J=8, 1.2, 2H); 8.35 (d, J=8, 1H).

Anal. Calc'd (C$_{26}$H$_{26}$ClO$_2$N): C, 74.36; H, 6.24; N, 3.34. Found: 74.17; 6.31; 3.31.

EXAMPLE 11
N-(2-[4,4',4"-Trichlorotrityl]oxyethyl)morpholine (5)

a. Dry DMSO (20 mL) was added to 14 mmol of hexane-washed KH under Ar with stirring at RT. After H$_2$ evolution ceased, a solution of tris-(p-chlorophenyl) methanol (3.63 g, 10 mmol) in 25 mL dry DMSO was added, giving a deep red anion solution. After 5 min, 1-bromo-3-methyl-2-butene (2.0 mL, 19 mmol) was added and stirring continued for 1 h. The crude product was isolated by Et$_2$O extraction and purified by flash chromatography (75 g SiO$_2$, 5% EtOAc-hexanes) giving 3.93 g (91%) of (3-methyl-2-butenyl) tris-(4-chlorophenyl)methyl ether as an oil.

NMR (CDCl$_3$): d 1.47, 1.72 (each s, 3H); 3.54 (d, 2H); 5.4 (t, 1H), 7.1–7.4 (m, 12H).

b. m-Chloroperoxybenzoic acid (80%, 2.15 g, 10 mmol) was added to a stirred suspension of 3.06 g (7.1 mmol) of the above allylic ether and 0.84 g (10 mmol) of NaHCO$_3$ in 50 mL of CH$_2$Cl$_2$. After 17 h, the mixture was diluted with EtOAc, washed with saturated Na$_2$CO$_3$, water (until neutral), brine, dried (MgSO$_4$) filtered and concentrated. The crude product was purified by flash chromatography (100 g SiO$_2$, 10% EtOAc-hexanes) giving 2.90 g (91%) of the epoxy ether as a white solid.

NMR (CDCl$_3$): d 1.13, 1.33 (each s, 3H); 3.03 (m, 1H, epoxy); 3.2 (m, 2H); 7.2–7.4 (m, 12H).

c. Periodic acid (1.90 g, 8.33 mmol) was added to a stirred solution of the above epoxy ether (2.87 g, 6.4 mmol) in 60 mL of dry Et$_2$O and 15 mL of CH$_2$Cl$_2$. After 1 h, the solution was washed with saturated NaHCO$_3$, water (until neutral), brine, dried (MgSO$_4$), filtered and concentrated giving 2.63 g of crude aldehyde as a foam. This material was dissolved at once in 60 mL of MeCN.

d. Morpholine (0.23 mL, 2.6 mmol) was added to a 12 mL portion of the above aldehyde/MeCN solution, followed by NaBH$_3$CN (0.25 g, 4.0 mmol). After 30 min the reaction was quenched with HOAc (2 mL), allowed to stand for 15 min, and poured into saturated Na$_2$CO$_3$. The crude product was isolated by EtOAc extraction and purified by flash chromatography (70 g SiO$_2$, 40% EtOAc-hexanes) giving 0.32 g of a solid. This material was recrystallized from EtOH, giving 0.21 g of (5), m.p. 151°–153° C. IR(KBr) 1490,1117,1093, 1066, 1014,817 cm$^{-1}$.

NMR (CDCl$_3$): d 2.46 (br t, J=4.6, 4H); 2.62 (t, J=6, 2H); 3.14 (t, J=6, 2H); 3.70 (br t, J=4.6, 4H); 7.3 (m, 12H).

Anal. Calc'd: C, 62.97; H, 5.07; N, 2.94. Found: 62.93; 5.06; 2.91.

EXAMPLE 12
1-(2[4,4',4"-Trichlorotrityl]oxyethyl)-4-(2-hydroxyethyl) piperazine dimaleate (6)

N-(2-hydroxyethyl)piperazine (0.32 mL, 2.6 mmol) was added to a 12 mL portion of the aldehyde/MeCN solution of Example 11(c). The mixture was quenched and extracted as above, and the crude free base dissolved in EtOH and treated with maleic acid (0.085 g, 0.73 mmol). The resulting solution was concentrated and triturated with $Et_2O$ giving a white solid, which was recrystallized (EtOH-EtOAc) to give 0.05 g of (6), m.p. 173°–176° C. (dec).

IR (KBr) 3409 (br), 1702 (w), 1616 (m), 1578, 1488, 1356, 1094, 920 $cm^{-1}$.

Anal. Calc'd ($C_{27}H_{29}N_2O_2Cl_3 \cdot [C_4H_4O_4]_2$): C, 55.89; H, 4.96; N, 3.73. Found: 55.72; 5.17; 3.73.

EXAMPLE 13
N-((2,6-Dichloro-3-methyl-phenyl)diphenyl) methylimidazole (16)

A solution of (2,6-dichloro-3-methylphenyl) diphenylmethanol (0.40 g, 1.2 mmol) and imidazole (0.50 g, 7.4 mmol) in 2 mL of acetic acid was heated to reflux for 2 h and then allowed to stand at RT for two days. The product was isolated by $EtOAc/H_2O$ partition followed by chromatography (75 g $SiO_2$, 50% EtOAc-hexane) to give 0.40 g (87%) of (16) as a white foam.

NMR ($CDCl_3$): d 2.36 (s, 3H); 6.56 (s, 1H); 7.3 (m, 12H); 7.83 (s, 1H).

EXAMPLE 14
Topical Ocular Formulation of Non-steroidal Glucocorticoid Antagonist

| Ingredient | Amount (wt. %) |
| --- | --- |
| Clotrimazole | 1.00 |
| Mannitol | 2.40 |
| Sodium Chloride | 0.40 |
| Carbopol 974P | 0.50 |
| Polysorbate 80 | 0.05 |
| Edetate Sodium | 0.01 |
| Benzalkonium Chloride | 0.01 |
| Sodium Hydroxide | Adjust pH to 7.2 |
| Purified Water | qs to 100% |

EXAMPLE 15
Formulation for Oral Administration

Tablet: 10–1000 mg of non-steroidal glucocorticoid antagonist with inactive ingredients such as cornstarch, lactose, colloidal silicon dioxide, microcrystalline cellulose, and magnesium stearate can be formulated according to procedures known to those skilled in the art of tablet formulation.

I claim:

1. A method for treating GLC1A glaucoma which comprises administering a pharmaceutically effective amount of a non-steroidal glucocorticoid antagonist.

2. The method of claim 1 wherein the non-steroidal glucocorticoid antagonist has the formula;

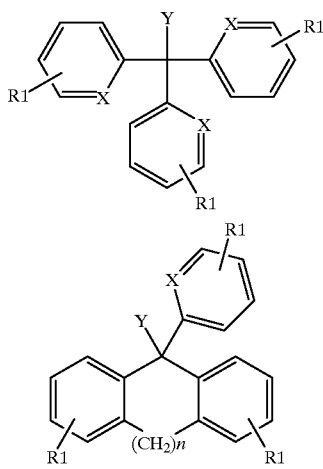

WHEREIN:

n=0,1,2;

X=CH or N;

R1=H, F, Cl, Br, R2, OR2, $N(R2)_2$, COOH, $CONH_2$, $CONHR_2$, $CON(R2)_2$, $CH_2N(CH_2CH_2)O$;

R2=$C_1$–$C_6$ alkyl;

Y=N-imidazolyl, N-pyrrolidinyl, N-(2-hydroxymethyl) pyrrolidinyl, N-triazolyl, N-pyrazolyl each optionally substituted with $CH_3$, SH or S—C(4-Cl—$C_6H_4$)$_3$; OH, $O(CH_2)_2N(CH_2CH_2)_2O$, $O(CH_2)_2N(CH_2CH_2)_2N(CH_2)_2OH$; and all pharmaceutically acceptable salts and esters.

3. The method of claim 2 wherein the non-steroidal glucocorticoid antagonist is selected from the group consisting of Clotrimazole; N-(Triphenylmethyl)imidazole; N-([2-Fluoro-9-phenyl]fluorenyl)imidazole; N-([2-Pyridyl] diphenylmethyl)imidazole; N-(2-[4,4',4"-Trichlorotrityl] oxyethyl)morpholine; 1-(2[4,4',4"-Trichlorotrityl] oxyethyl)-4-(2-hydroxyethyl)piperazine dimaleate; N-([4,4', 4"]-Trichlorotrityl)imidazole; 9-(3-Mercapto-1,2,4-trazolyl)-9-phenyl-2,7-difluorofluorenone; 1-(2-Chlorotrityl)-3,5-dimethylpyrazole; 4-(Morpholinomethyl)-A-(2-pyridyl)benzhydrol; 5-(5-Methoxy-2-(N-methylcarbamoyl)-phenyl)dibenzosuberol; N-(2-Chlorotrityl)-L-prolinol acetate; 1-(2-Chlorotrityl)-2-methylimidazole; 1-(2-Chlorotrityl)-1,2,4-triazole; 1,S-Bis (4,4',4"-trichlorotrityl)-1,2,4-triazole-3-thiol; and N-((2,6-dichloro-3-methylphenyl)diphenyl) methylimidazole.

4. The method of claim 1 wherein the non-steroidal glucocorticoid antagonist is ketoconazole.

* * * * *

UNITED STATES PATENT AND TRADEMARK OFFICE
CERTIFICATE OF CORRECTION

PATENT NO : 6,051,573
DATED : April 18, 2000
INVENTOR(S) : CLARK, Abbot F.

It is certified that error appears in the above-identified patent and that said Letters Patent are hereby corrected as shown below:

Title page, item [63], change continuation-in-part of application No. 08/631,041 to continuation of application No. 08/631,041.

Signed and Sealed this

Twenty-second Day of May, 2001

Attest:

NICHOLAS P. GODICI

Attesting Officer     Acting Director of the United States Patent and Trademark Office